United States Patent [19]

Harashima et al.

[11] Patent Number: 5,628,989
[45] Date of Patent: May 13, 1997

[54] ANTIPERSPIRANT AND DEODORANT

[75] Inventors: Asao Harashima, Tokyo; Yoshitsugu Morita; Ryuji Tachibana, both of Chiba Prefecture, all of Japan

[73] Assignee: Dow Corning Toray Silicone Co., Ltd., Tokyo, Japan

[21] Appl. No.: 489,474

[22] Filed: Jun. 12, 1995

[30] Foreign Application Priority Data

Jun. 30, 1994 [JP] Japan .................................. 6-173618

[51] Int. Cl.$^6$ .................. A61K 7/32; A61K 7/34; A61K 7/38
[52] U.S. Cl. .................. 424/65; 424/66; 424/68; 424/78.02; 424/78.05; 424/78.07; 424/400; 424/401; 424/DIG. 5
[58] Field of Search .................. 424/65, 66, 68, 424/400, 401, DIG. 5, 78.02, 78.05, 78.07

[56] References Cited

U.S. PATENT DOCUMENTS 4,980,167  12/1990  Harashima ........................ 424/401

OTHER PUBLICATIONS

JIS K 6301, Japanese Industrial STANDARD, Hardness Test, JIS A, pp. 1,2 and 10–15, cited for informational purposes.

*Primary Examiner*—Shelley A. Dodson
*Attorney, Agent, or Firm*—James L. DeCesare

[57] ABSTRACT

Antiperspirant/deodorants contain 5–90 wt % of spheroid silicone rubber powders with average particle sizes of 0.1–200 μm and JIS A hardness of the silicone rubber forming said powder is 35–80. They spread well, are smooth, and have a dry feel when used.

5 Claims, No Drawings

ANTIPERSPIRANT AND DEODORANT

BACKGROUND OF THE INVENTION

This invention concerns antiperspirant/deodorants. Specifically, it concerns antiperspirant/deodorants that spread well, are smooth and feel dry when used.

Antiperspirant/deodorants control perspiration and are used to prevent body odor of underarms caused by degradation of sweat by microorganisms such as normal skin flora. Generally, astringents for suppressing perspiration by protein constricting effects or antimicrobial or microbicidal agents for suppressing growth of microorganisms are blended into antiperspirants/deodorants. For fillers that improve adhesion to skin and give a pleasant feel when used, clay minerals such as talc (see Japanese Kokai Patent Application No. Sho 62[1987]-164615) or spherical polyorganosilsesquioxane powders (see Japanese Kokai Patent Application No. Hei 5[1993]-39215) are blended.

However, since fillers such as talc or other clay minerals and polyorganosilsesquioxane powders are very hard, antiperspirant/deodorants made by blending these have a squeaky feel or gritty foreign substance sensation. Moreover, there was the problem that these tended to cause contact dermatitis in susceptible skin.

SUMMARY OF THE INVENTION

Upon earnest studies to solve the above problems, tile inventors arrived at this invention. That is, the goal of this invention is to present antiperspirant/deodorants that spread well, are smooth and have a dry feel when used.

DETAILED DESCRIPTION OF THE INVENTION

The antiperspirant/deodorants of this invention are characterized by the fact that they contain 5–90 wt % of spheroid silicone rubber powder of 0.1–200 μm average particle size provided the JIS A hardness of the silicone rubber forming said powder is 35–80. The antiperspirant/deodorants of this invention are explained in detail below.

The compositions of the antiperspirant/deodorants of this invention differ in their formulation. The formulations are not particularly restricted; for example, liquids, creams, waxes and powders can be used.

For the silicone rubber powders that are the essential components in the antiperspirant/deodorants of this invention, their average particle sizes must be in the range of 0.1–200 μm. This is because it is difficult to manifest the effects of this invention if silicone rubber powder with average particle sizes of less than 0.1 μm are used and there is a squeaky feel or lumpy foreign substance sensation if silicone rubber powders in which these sizes exceed 200 μm are used. Moreover, the feel when used tends to improve as the range of particle sizes of this silicone rubber powder is reduced, and to obtain ideal feel during use, it is preferable that this particle diameter is less than 250 μm. It is necessary that the shape of this silicone rubber powder is spheroid but it need not be strictly spherical. It can, for example, be spheroid with oval cross-sections, but, spherical shapes are preferable. Moreover, it is necessary that the JIS A hardness (stipulated in JIS K 6301) of the silicone rubber forming this silicone rubber powder is in the range of 35–80. This is because the composition starts to feel sticky if powders formed from silicone rubbers for which JIS A hardness is less than 35 are used, and it starts to feel gritty and have a foreign substance sensation when powders formed from silicone rubbers for which this hardness exceeds 80 are used.

The method for producing these silicone rubber powders is not particularly limited. For example, the method of spraying heat-curable liquid silicone rubber compositions into hot air and curing so that they become spheroids with average particle sizes of 0.1–200 μm, and the method of dispersing heat-curable liquid silicone rubber compositions into water so that they become spheroids with average particle sizes of 0.1–200 μm and curing (see Japanese Kokai Patent Application No. Sho 63[1988]-77942, Japanese Kokai Patent Application No. Sho 64[1989]-70558) can be used. The latter method is preferable because average particle sizes are small, the range of particle sizes is narrow and spheroid silicone rubber powders can be prepared.

In the antiperspirant/deodorants of this invention, the amount blended of this silicone rubber powder differs with the formulation. But generally, it must be in the range of 5–90 wt %. The range of 10–80 wt % is particularly preferable. This is because it is difficult to manifest the effects of this invention if the amount blended of this silicone rubber powder is less than 5 wt % and if it exceeds 90 wt %, stability of the formulations decreases when made into creams or sticks, or usability as antiperspirant/deodorants is reduced.

In the antiperspirant/deodorants of this invention, astringents to suppress perspiration can also be blended. For these astringents, well-known compounds in antiperspirant/deodorants can be used. Aluminum chlorohydroxide aluminum hydroxybromide, aluminum chloride, aluminum/zirconium/glycine complexes, mixtures of aluminum chloride with aluminum hydroxychloride or aluminum chlorohydroxide can be used for these astringents. In the antiperspirant/deodorants of this invention, these astringents can be blended alone or as mixtures of 2 or more.

The amount blended of these astringents in the antiperspirant/deodorants of this invention is optional, but to obtain satisfactory antiperspirant effects, formulation stability and pleasant feel during use, it is preferably in the range of 1–50 wt %. The range of 5–30 wt % is particularly preferable.

Moreover, in the antiperspirant/deodorants of this invention, antimicrobial or microbicidal agents for suppressing the growth of microorganisms such as normal skin flora which degrade sweat and cause body odor can be blended. For these antimicrobial and microbicidal agents, compounds that are well-known in antiperspirant/deodorants can be used. Quaternary ammonium salts, alkyldiaminoethyl glycine chloride solutions, isopropylmethylphenol, and Triclosan (trichlorohydroxydiphenyl ether) can be used for these antimicrobial and microbicidal agents. In the antiperspirant/deodorants of this invention, these antimicrobial or microbicidal agents can be blended alone or as mixtures of 2 or more.

The amount blended of these antimicrobial or microbicidal agents in the antiperspirant/deodorants is optional, but to obtain satisfactory antimicrobial or microbicidal effects, formulation stability and good feel during use, it is preferably in the range of 0.01–10 wt %. The range of 0.1–5 wt % is particularly preferable.

In the antiperspirant/deodorants of this invention, for example, waxes of 50°–110° C. melting point can be blended as lipid components to give good adhesion and to keep the formulation semisolid or solid. Beeswax, carnauba wax, candelilla wax, ozocerite, ceresin, rice wax, vegetable wax, montan wax, paraffin, microcrystalline wax, stearyl alcohol, hardened castor oil, lanolin, Vaseline, and cholesteryl stearate can be used for these waxes. Semisolid or solid silicone oils such as alkoxy-modified polysiloxane, polyoxyalkylene-modified silicone or alkyl-modified silicones can also be used. In the antiperspirant/deodorants of this invention, these waxes can be blended alone or as mixtures of 2 or more.

Moreover, in the antiperspirant/deodorants of this invention, for example, oil components that are liquid at room temperature can be blended as oil components for giving good adhesion or to keep the formulation in cream or liquid form. Some examples are liquid paraffin, hexyl laurate, isopropyl myristate, myristyl myristate, cetyl myristate, 2-octyldodecyl myristate, isopropyl palmitate, 2-ethylhexyl palmitate, butyl stearate, decyl oleate, 2-octyldodecyl oleate, myristyl lactate, cetyl lactate, lanolin acetate, stearyl alcohol, cetostearyl alcohol, oleyl alcohol, avocado oil, almond oil, olive oil, cacao oil, jojoba oil, sesame oil, safflower oil, soybean oil, camellia oil, squalane, castor oil, mink oil, cottonseed oil, coconut oil, beef fat, pork fat, glycol ester oils such as polypropylene glycol monooleate or neopentyl glycol 2-ethylhexanoate; polyoxyalkylene ether oils such as polyoxyethylene lauryl ether or polyoxypropylene cetyl ether; alcohols such as ethanol, octyl dodecanol, cetyl alcohol or oleyl alcohol; and silicone oils such as dimethylsiloxane, polymethylphenylsiloxane, polymethylhydrogensiloxane, dimethylsiloxane methylstearoxysiloxane copolymers, dimethylsiloxane methylcetyloxysiloxane copolymers, dimethylsiloxane methyl (polyoxyethyl)siloxane copolymers, dimethylsiloxane methyl(polyoxyethylene-polyoxypropylene)siloxane copolymers, dimethylsiloxane-methyl(polyoxypropylene) siloxane copolymers, cyclic polydimethylsiloxane, cyclic polymethylphenylsiloxane, cyclic polymethylhydrogensiloxane, amino-modified polysiloxane, epoxy-modified polysiloxane, polyoxyalkylene-modified polysiloxane, alkoxy-modified polysiloxane, and alkyl-modified polysiloxane. In the antiperspirant/deodorants of this invention, these oil components can be blended alone or as mixtures of 2 or more.

The amounts blended of waxes with melting points of 50°–110° C. or of oil components that are liquid at room temperature in the antiperspirant/deodorants of this invention are optional, but to give good adhesion and maintain the formulation, they are preferably in the range of 0.5–90 wt %. The range of 1–80 wt % is particularly preferable.

In the antiperspirant/deodorants of this invention, volatile oils can be blended to give good adhesion and give a refreshing feel during and after use. Cyclic diorganosiloxanes such as octamethyltetracyclosiloxane, decamethylcyclopentasiloxane, dodecamethylcyclohexasiloxane; diorganosiloxane oligomers such as hexamethyldisiloxane, octamethyltrisiloxane, decamethyltetrasiloxane; low-order alcohols such as methyl alcohol, ethyl alcohol, n-propyl alcohol, and isopropyl alcohol as well as paraffinic hydrocarbons can be used for these volatile oils. In the antiperspirant/deodorants of this invention, these volatile oils can be blended alone or as mixtures of 2 or more.

The amount blended of these volatile oils in the antiperspirant/deodorants of this invention is optional, but to give good adhesion and a refreshing feel, it is preferably in the range of 0.5–90 wt %. The range of 1–80 wt % is particularly preferable.

In the antiperspirant/deodorants of this invention, fillers that are normally used to improve adhesion to the skin can be blended. Talc, mica, colloidal silica, kaolin, zinc oxide, magnesium carbonate, calcium carbonate, bentonite, hectorite, colloidal aluminum magnesium silicate, silk powder, polyethylene resin powders, Teflon powder, acrylic resin powder, polypropylene resin powders, polystyrene resin powders, vinyl chloride resin powder, cellulose powder, nylon resin powders, and polyorganosilsesquioxane powders can be used for such fillers. These fillers can be blended in the antiperspirant/deodorants of this invention alone or as mixtures of 2 or more.

The amount blended of these fillers in the antiperspirant/deodorants of this invention is optional, but to obtain adhesion to skin, formulation stability and good usability, it is preferably in the range of 5–90 wt %. The range of 10–80 wt % is particularly preferable.

Moreover, purified water can be blended into the antiperspirant/deodorants of this invention to make these into emulsions. The above oil components can be emulsified or surfactants can be blended so that the oils can be easily washed off with water after use. Sorbitan aliphatic esters, polyoxyethylene sorbitol lanolin derivatives, polyoxyethylene aliphatic ethers, polyoxyethylene propylene glycol stearate, polyoxyethylene stearate, polyoxyethylene sorbitan aliphatic ethers and polyoxypropylene-polyoxyethylene condensates can be used for these surfactants. In the antiperspirant/deodorants of this invention, these surfactants can be blended alone or as mixtures of 2 or more. Moreover, dyes, pigments, fragrances, anti-inflammatory agents, moisturizers, antioxidants, stabilizers and preservatives can be blended as other optional components in the antiperspirant/deodorants of this invention depending on the application.

The antiperspirant/deodorants of this invention can be formulations such as solids, semisolids, creams, liquids or powders, and depending on their formulation, they are applied to the skin by spraying or as sticks or roll-ons. When using the antiperspirant/deodorants of this invention as sticks, they can be prepared by heating liquid oil components, waxes, silicone rubber powder, astringents, antimicrobial or microbicidal agents, and other optional components above the melting point of said waxes, and stirring to homogeneity and then cooling to room temperature in stick molds.

The method for preparing the antiperspirant/deodorants of this invention is not particularly restricted. For example, they can be prepared by batch modes or continuous modes. Moreover, the devices for preparing the antiperspirant/deodorants of this invention are not particularly restricted. For example, homomixers, paddle mixers, colloid mills, propeller stirrers, homogenizers, in-line continuous emulsifiers, ultrasound emulsifiers and vacuum kneaders can be used.

The antiperspirant/deodorants of this invention are explained in detail with application examples. In the application examples, viscosity is the value measured at 25° C. JIS A hardness of the silicone rubber, particle size and shape of the silicone rubber powder and functional evaluation of the antiperspirant/deodorants were measured as follows.

The raw material silicone rubber composition was heated for 1 h in a 150° C. hot air convection oven to prepare the silicone rubber. After cooling this to room temperature, hardness was measured with a JIS A hardness meter prescribed in JIS K 6301.

The particle size of the silicone rubber powder was measured with an image-processing device connected to an optical microscope, and its maximum particle size and average particle size were determined. The shape of the silicone rubber powder was observed with a scanning electron microscope.

The spreading, adhesion and feel during use of the antiperspirant/deodorants were evaluated functionally by 10 panelists. When 8 or more people judged the property to be good, it was rated as O, when 4–7 people judged it to be good, it was rated as Δ and when less than 4 people judged it to be good, it was rated as X.

REFERENCE EXAMPLE 1

100 parts by weight of polydimethylsiloxane in which both ends of the molecular chain were blocked with dimethylvinylsiloxy groups (vinyl group equivalents=2,500), 5.2 parts by weight of polymethylhydrogensiloxane of 20 cP viscosity in which both the molecular chain ends were blocked with trimethylsiloxy groups and an isopropanol solution of chloroplatinate (an amount such that platinum metal would be 50 ppm with respect to the weight of this composition) were mixed to homogeneity at 5° C. to prepare a liquid silicone rubber composition. After this liquid silicone rubber composition was quickly mixed into 300 parts by weight of a 2 wt % aqueous solution of 25° C. pure water (conductivity 0.2 µS/cm) and polyoxyethylene (9 mol added) lauryl ether, this was passed through a homogenizer (300 kgf/cm²) to prepare a homogeneous aqueous dispersion of the liquid silicone rubber composition. This aqueous dispersion was left undisturbed for 6 hours at 30° C., then heated for 1 hour at 80° C. to cure said composition. The aqueous dispersion was dried with a spray dryer and silicone rubber powder (A) was prepared. The characteristics of silicone rubber powder (A) are shown in Table I.

REFERENCE EXAMPLE 2

100 parts by weight of polydimethylsiloxane in which both ends of the molecular chain were blocked with dimethylvinylsiloxy groups (vinyl group equivalents=2500), 5.2 parts by weight of polymethylhydrogensiloxane of 20 cP viscosity in which both the molecular chain ends were blocked with trimethylsiloxy groups and an isopropanol solution of chloroplatinate (an amount such that platinum metal would be 50 ppm with respect to the weight of this composition) were mixed to homogeneity at 5° C. to prepare a liquid silicone rubber composition. After this liquid silicone rubber composition was quickly mixed into 300 parts by weight of a 2 wt % aqueous solution of 25° C. pure water (conductivity 0.2 µS/cm) and polyoxyethylene (9 mol added) lauryl ether, this was passed through a 1 mm gap colloid mill to prepare a homogeneous aqueous dispersion of the liquid silicone rubber composition. This aqueous dispersion was left undisturbed for 6 h at 30° C., then heated for 1 hour at 80° C. to cure said composition. The aqueous dispersion was dried with a spray dryer and silicone rubber powder (B) was prepared. The characteristics of silicone rubber powder (B) are shown in Table I.

REFERENCE EXAMPLE 3

100 parts by weight of polydimethylsiloxane in which both ends of the molecular chain were blocked with dimethylvinylsiloxy groups (vinyl group equivalents=5000), 4.5 parts by weight of dimethylsiloxanemethylhydrogensiloxane copolymer in which both the molecular chain ends were blocked with trimethylsiloxy groups and an isopropanol solution of chloroplatinate (an amount such that platinum metal would be 50 ppm with respect to the weight of this composition) were mixed to homogeneity at 5° C. to prepare a liquid silicone rubber composition. After this liquid silicone rubber composition was quickly mixed into 300 parts by weight of a 2 wt % aqueous solution of 25° C. pure water (conductivity 0.2 µS/cm) and polyoxyethylene (9 mol added) lauryl ether, this was passed through a homogenizer (300 kgf/cm²) to prepare a homogeneous aqueous dispersion of the liquid silicone rubber composition. This aqueous dispersion was left undisturbed for 6 hours at 30° C., then heated for 1 h at 80° C. to cure said composition. The aqueous dispersion was dried with a spray dryer and silicone rubber powder (C) was prepared. The characteristics of silicone rubber powder (C) are shown in Table I.

REFERENCE EXAMPLE 4

100 parts by weight of polydimethylsiloxane in which both ends of the molecular chain were blocked with dimethylvinylsiloxy groups (vinyl group equivalents=5000), 4.5 parts by weight of dimethylsiloxanemethylhydrogensiloxane copolymer in which both the molecular chain ends were blocked with trimethylsiloxy groups, 50 parts by weight of dimethylpolysiloxane of 100 [sic] viscosity in which both the molecular ends were blocked with trimethylsiloxy groups and an isopropanol solution of chloroplatinate (an amount such that platinum metal would be 50 ppm with respect to the weight of this composition) were mixed to homogeneity at 5° C. to prepare a liquid silicone rubber composition. After this liquid silicone rubber composition was quickly mixed into 300 parts by weight of a 2 wt % aqueous solution of 25° C. pure water (conductivity 0.2 µS/cm) and polyoxyethylene (9 mol added) lauryl ether, this was passed through a homogenizer (300 kgf/cm²) to prepare a homogeneous aqueous dispersion of the liquid silicone rubber composition. This aqueous dispersion was left undisturbed for 6 h at 30° C., then heated for 1 h at 80° C. to cure said composition. The aqueous dispersion was dried with a spray dryer and silicone rubber powder (D) was prepared. The characteristics of this silicone rubber powder (D) are shown in Table I.

REFERENCE EXAMPLE 5

100 parts by weight of polydimethylsiloxane in which both ends of the molecular chain were blocked with dimethylvinylsiloxy groups (vinyl group equivalents=2500), 5.2 parts by weight of polymethylhydrogensiloxane of 20 cP viscosity in which both the molecular chain ends were blocked with trimethylsiloxy groups and an isopropanol solution of chloroplatinate (an amount such that platinum metal would be 50 ppm with respect to the weight of this composition) were mixed to homogeneity at 5° C. to prepare a liquid silicone rubber composition. This liquid silicone rubber composition was heated for 1 h in a 150° C. hot air convection oven to cure said composition. The aqueous dispersion was finely ground in a crusher for 3 h and silicone rubber powder (E) that passed through a 100 mesh sieve was prepared. The characteristics of this silicone rubber powder (E) are shown in Table I.

TABLE I

| EXAMPLE | 1 | 2 | 3 | 4 | 5 |
|---|---|---|---|---|---|
| POWDER | A | B | C | D | E |
| PARTICLE SIZE (Maximum Microns) | 30 | 700 | 50 | 50 | 150 |
| PARTICLE SIZE (Average Microns) | 3 | 250 | 4 | 5 | 70 |
| HARDNESS (JIS A) | 48 | 48 | 26 | 15 | 48 |
| SHAPE | Spherical | Spheroid | Spherical | Spherical | Amorphous |

APPLICATION AND COMPARATIVE EXAMPLE 6

30 wt % of the various silicone rubber powders (A–E) prepared in Reference Examples 1–5 above, and a polymethylsilsesquioxane powder (F) of 3 μm average particle size and 90 JIS A hardness, 25 wt % of isopropyl myristate, 23.9 wt % of decamethylcyclopentasiloxane, 20 wt % aluminum hydroxychloride, 0.1 wt % Triclosan and 1 wt % of fragrance, were mixed to homogeneity at room temperature in a propeller stirrer to prepare antiperspirant/deodorants. And for comparison, antiperspirant/deodorant was prepared using talc surface-treated with dimethylpolysiloxane instead of the silicone rubber powder. These antiperspirant/deodorants were sprayed on the skin of panelists and evaluated functionally. Those results are shown in Table II.

TABLE II

| Powder | NONE | A | B | C | D | E | F |
|---|---|---|---|---|---|---|---|
| Spreadings | O | O | Δ | Δ | X | X | O |
| Adhesion | Δ | O | X | O | Δ | X | Δ |
| Feel | X | O | X | X | Δ | X | X |
| During Use | Gritty Sticky | Smooth Dry | Lumpy | Gritty Sticky | Gritty Sticky | Lumpy | Gritty |

The antiperspirant/deodorants of this invention have the characteristics that they spread well and have a dry feel during use.

Table II shows that the underarm composition containing powder A was the best of the seven compositions evaluated. As shown in Table I, powder A had a maximum particle size of less than 5 microns (i.e. 3 microns).

Other variations and modifications may be made in the compositions described without departing from the essential features of the invention. The forms of the invention are only exemplary and not intended as limitations on the scope of the invention defined in the claims.

That which is claimed is:

1. A composition for application to the underarm comprising 5–90% by weight based on the weight of the composition of a silicone rubber powder which is free of silicone oil, the silicone rubber powder having an average particle size of 0.1–200 microns and a JIS A hardness of 35–80; the remainder of the composition comprising an oil, a cyclic diorganosiloxane, an astringent selected from the group consisting of aluminum chlorohydroxide, aluminum hydroxybromide, aluminum chloride, aluminum/zirconium/glycine complexes, mixtures of aluminum chloride with aluminum hydroxychloride, and mixtures of aluminum chloride with aluminum chlorohydroxide, and an antimicrobial agent selected from the group consisting of quaternary ammonium salts, alkyldiaminoethyl glycine chloride solutions, isopropylmethylphenol, and trichlorohydroxydiphenyl ether.

2. A composition for application to the underarm according to claim 1 in which the silicone rubber powder is spherical and has a maximum particle size of less than 250 microns but an average particle size of less than 5 microns.

3. A composition for application to the underarm comprising 5–90% by weight based on the weight of the composition of a silicone rubber powder which is free of silicone oil, the silicone rubber powder having an average particle size of 0.1–200 microns and a JIS A hardness of 35–80; 0.5–90% by weight of an oil; 0.5–90% by weight of a cyclic diorganosiloxane; 1–50% by weight of an astringent selected from the group consisting of aluminum chlorohydroxide, aluminum hydroxybromide, aluminum chloride, aluminum/zirconium/glycine complexes, mixtures of aluminum chloride with aluminum hydroxychloride, and mixtures of aluminum chloride with aluminum chlorohydroxide; and 0.01–10% by weight of an antimicrobial agent selected from the group consisting of quaternary ammonium salts, alkyldiaminoethyl glycine chloride solutions, isopropylmethylphenol, and trichlorohydroxydiphenyl ether.

4. A composition for application to the underarm according to claim 3 in which the silicone rubber powder is spherical and has a maximum particle size of less than 250 microns but an average particle size of less than 5 microns.

5. A composition for application to the underarm comprising 5–90% by weight based on the weight of the composition of a spherical silicone rubber powder which is free of silicone oil, the silicone rubber powder having a maximum particle size of less than 50 microns but an average particle size of less than 5 microns, and a JIS A hardness of 35–80; 0.5–90% by weight of an oil; 0.5–90% by weight of a cyclic diorganosiloxane; 1–50% by weight of an astringent selected from the group consisting of aluminum chlorohydroxide, aluminum hydroxybromide, aluminum chloride, aluminum/zirconium/glycine complexes, mixtures of aluminum chloride with aluminum hydroxychloride, and mixtures of aluminum chloride with aluminum chlorohydroxide; and 0.01–10% by weight of an antimicrobial agent selected from the group consisting of quaternary ammonium salts, alkyldiaminoethyl glycine chloride solutions, isopropylmethylphenol, and trichlorohydroxydiphenyl ether.

* * * * *